US012295602B2

(12) United States Patent
Algawi et al.

(10) Patent No.: US 12,295,602 B2
(45) Date of Patent: May 13, 2025

(54) MEDICAL PROBE HAVING IMPROVED MANEUVERABILITY

(71) Applicant: Biosense Webster (Israel) Ltd., Yokneam (IL)

(72) Inventors: Yehuda Algawi, Binyamina (IL); Assaf Govari, Haifa (IL); Ilya Sitnitsky, Nahariya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 330 days.

(21) Appl. No.: 17/539,336

(22) Filed: Dec. 1, 2021

(65) Prior Publication Data

US 2022/0160385 A1    May 26, 2022

Related U.S. Application Data

(63) Continuation of application No. 16/421,430, filed on May 23, 2019, now Pat. No. 11,213,309.

(51) Int. Cl.
| | |
|---|---|
| *A61M 25/00* | (2006.01) |
| *A61B 17/24* | (2006.01) |
| *A61B 18/22* | (2006.01) |
| *A61B 1/233* | (2006.01) |
| *A61B 18/00* | (2006.01) |

(Continued)

(52) U.S. Cl.
CPC ............. *A61B 17/24* (2013.01); *A61B 18/22* (2013.01); *A61B 1/233* (2013.01); *A61B 2018/00202* (2013.01); *A61B 2018/20357* (2017.05); *A61M 25/005* (2013.01); *A61M 25/0147* (2013.01)

(58) Field of Classification Search
CPC ..... A61B 1/0055; A61B 1/0056; A61B 1/233; A61M 25/0147; A61M 25/0054
See application file for complete search history.

(56) References Cited

U.S. PATENT DOCUMENTS

| | | |
|---|---|---|
| 5,304,131 A | 4/1994 | Paskar |
| 5,391,199 A | 2/1995 | Ben-Haim |

(Continued)

FOREIGN PATENT DOCUMENTS

| | | |
|---|---|---|
| CN | 108013861 A | 5/2018 |
| EP | 2777476 A1 | 9/2014 |

(Continued)

OTHER PUBLICATIONS

International Search Report and Written Opinion dated Aug. 6, 2020, for International Application No. PCT/IB2020/053935, 12 pages.

(Continued)

*Primary Examiner* — Deanna K Hall
(74) *Attorney, Agent, or Firm* — Frost Brown Todd LLP

(57) ABSTRACT

A medical probe includes a shaft for insertion into a cavity of a patient body, and a distal-end assembly. The distal-end assembly is coupled to a distal end of the shaft and includes a hollow tube having (i) a first opening, located at a first section along a longitudinal axis of the hollow tube, and having a first size that limits bending of the first section by a first local radius of curvature (LROC), and (ii) a second opening, located at a second different section along the longitudinal axis of the hollow tube, and having a second different size that limits bending of the second section by a second different LROC.

20 Claims, 3 Drawing Sheets

(51) Int. Cl.
 *A61B 18/20* (2006.01)
 *A61M 25/01* (2006.01)

(56) References Cited

U.S. PATENT DOCUMENTS

| | | |
|---|---|---|
| 5,437,288 A | 8/1995 | Schwartz et al. |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 6,749,560 B1 | 6/2004 | Konstorum et al. |
| 9,402,682 B2 | 8/2016 | Worrell et al. |
| 9,795,765 B2 | 10/2017 | Romoscanu |
| 10,226,185 B2 | 3/2019 | Ranganathan et al. |
| 11,213,309 B2 | 1/2022 | Algawi et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2005/0020974 A1 | 1/2005 | Noriega et al. |
| 2010/0331883 A1 | 12/2010 | Schmitz et al. |
| 2011/0152880 A1 | 6/2011 | Alvarez et al. |
| 2014/0053940 A1 | 2/2014 | Konstorum et al. |
| 2014/0135736 A1 | 5/2014 | Hebert |
| 2017/0112669 A1 | 4/2017 | Scheller et al. |
| 2017/0325841 A1* | 11/2017 | Govari ............... A61B 1/0052 |
| 2018/0042451 A1* | 2/2018 | Cuscuna ............. A61B 8/12 |
| 2018/0311465 A1 | 11/2018 | Algawi et al. |
| 2018/0311470 A1 | 11/2018 | Algawi et al. |

FOREIGN PATENT DOCUMENTS

| | | |
|---|---|---|
| EP | 3138465 A1 | 3/2017 |
| EP | 3192428 A1 | 7/2017 |
| EP | 3254609 A2 | 12/2017 |
| WO | WO 1996/005768 A1 | 2/1996 |

OTHER PUBLICATIONS

Chinese First Office Action and Search Report dated Sep. 14, 2024, for Application No. 202080038307.4, 9 pages.
Japanese First Office Action dated Feb. 20, 2024, for Application No. 2021-569448, 5 pages.
Japanese Final Office Action dated Jul. 30, 2024, for Application No. 2021-569448, 3 pages.

* cited by examiner

MEDICAL PROBE HAVING IMPROVED MANEUVERABILITY

This application is a continuation of U.S. patent application Ser. No. 16/421,430, entitled "Medical Probe Having Improved Maneuverability," filed May 23, 2019, issued as U.S. Pat. No. 11,213,309 on Jan. 4, 2022.

FIELD OF THE INVENTION

The present invention relates generally to minimally invasive medical devices, and particularly to techniques for medical probes having improved maneuverability.

BACKGROUND OF THE INVENTION

Various types of medical probes have mechanical designs intended to improve probe maneuverability in a patient body.

For example, U.S. Patent Application Publication 2017/0112669, issued as U.S. Pat. No. 7,775,745 on Oct. 3, 2017, describes a steerable laser probe that may include a handle, and inner bore of the handle, an actuation lever of the handle, a housing tube, and an optic fiber disposed within the inner bore of the handle and the housing tube. The housing tube may have a first housing tube portion having a first stiffness and a second housing tube portion having a second stiffness. The second stiffness may be greater than the first stiffness.

U.S. Patent Application Publication 2011/0152880, now abandoned, describes an instrument for performing minimally invasive surgical procedures. The instrument includes an elongate body and a support member disposed within or along the elongate body. The support member is configured to support steering, articulation, and angular rotational movement of the elongate body, provide torsion control, and support precise and accurate placement of the distal portion of the elongate body so that complex surgical procedure may be performed using the instrument.

U.S. Patent Application Publication 2014/0135736, issued as U.S. Pat. No. 9,233,225 on Jan. 12, 2016, describes a deflectable catheter that includes an outer member having a proximal portion and a distal portion, an elongated column member extending distally from the outer member and an inner member positioned coaxial with the outer member and attached to the column member. The inner member extends distally of the outer member and has a distal tip portion.

SUMMARY OF THE INVENTION

An embodiment of the present invention that is described herein provides a medical probe including a shaft for insertion into a cavity of a patient body, and a distal-end assembly. The distal-end assembly is coupled to a distal end of the shaft and includes a hollow tube having (i) a first opening, located at a first section along a longitudinal axis of the hollow tube, and having a first size that limits bending of the first section by a first local radius of curvature (LROC), and (ii) a second opening, located at a second different section along the longitudinal axis of the hollow tube, and having a second different size that limits bending of the second section by a second different LROC.

In some embodiments, the first opening includes a first slit having a first opening angle, and the second opening includes a second slit having a second opening angle, different from the first opening angle. In other embodiments, the first section is distal to the second section, the first opening is larger than the second opening, and the first LROC is smaller than the second LROC. In yet other embodiments, at least the first section includes a first protrusion, at least the first opening includes a first intrusion, and the first intrusion is sized and shaped to snugly fit over the first protrusion.

In an embodiment, the medical probe includes a control handle, fitted at a proximal end of the shaft and configured to bend the first section by up to the first LROC and the second section by up to the second LROC. In another embodiment, the medical probe includes a pull wire, which is coupled, at a first end to the control handle, and at a second end to a selected section of the distal-end assembly, and the control handle is configured to bend at least one of the first section and the second section, by pulling the first end of the pull wire. In yet another embodiment, the pull wire includes an alloy of nickel and titanium.

In some embodiments, the control handle is configured to bend one of the first section and the second section relative to the longitudinal axis, and simultaneously, to maintain the other of the first section and the second section flush with the shaft. In other embodiments, the cavity comprises an ear-nose-throat (ENT) sinus.

There is additionally provided, in accordance with an embodiment of the present invention, a method for producing a medical probe, the method includes providing a shaft for insertion into a cavity of a patient body. A distal-end assembly that includes a hollow tube is coupled to a distal end of the shaft. The hollow tube has (i) a first opening, located at a first section along a longitudinal axis of the hollow tube, and having a first size that limits bending of the first section by a first local radius of curvature (LROC), and (ii) a second opening, located at a second different section along the longitudinal axis of the hollow tube, and having a second different size that limits bending of the second section by a second different LROC.

In some embodiments, the method includes forming at least one of the first and second opening using a laser cutting technique.

The present invention will be more fully understood from the following detailed description of the embodiments thereof, taken together with the drawings in which:

DETAILED DESCRIPTION OF EMBODIMENTS

Overview

Various medical procedures require the insertion of a medical probe into an organ of a patient. Probe maneuvering within branched human organs, such as a sinus of a patient ear-nose-throat (ENT) system, to a desired location and at the correct orientation, is typically challenging. Moreover, external forces applied, e.g., by the internal surface of the patient nostril, may complicate the insertion process.

Embodiments of the present invention that are described hereinbelow provide a medical probe having improved maneuverability by using a flexible distal-end assembly.

In some embodiments, the medical probe comprises a shaft for insertion into a cavity of a patient body, such as a sinus of a patient ENT system, and the distal-end assembly is coupled to the distal end of the shaft. The distal-end assembly comprises a hollow tube having at least two openings, wherein each of these openings is located at a different section along the hollow tube. The openings provide a bending ability to the tube. The maximal bending ability at a given location along the tube is specified by a local radius of curvature (LROC) at that location.

In some embodiments, a first opening, which is located at a first, distalmost, section of the hollow tube, has a given size that limits the bending ability of the distalmost section by a predefined LROC. In some embodiments, a second opening, which is located along the hollow tube at a second section, proximal to the first section, has a size smaller than the given size, resulting in a LROC larger than the predefined LROC of the first section. In some embodiments, the hollow tube may comprise multiple (e.g., ten) openings formed along the longitudinal axis of the tube, wherein the size of the openings increases with the proximity to the distal end of the tube. Thus, the LROC corresponding to the openings decreases with their proximity to the distal end of the tube.

In some embodiments, the distal-end assembly comprises a control handle fitted at the proximal end of the shaft. The distal-end assembly further comprises a pull wire, which runs through a longitudinal lumen of the tube, and is coupled to the distalmost section of the hollow tube and to the control handle. In some embodiments, in performing an ENT procedure, the physician may bend one or more sections of the distal-end assembly up to the desired respective LROCs, by pulling or retracting the pull wire.

The disclosed techniques improve the insertion and maneuverability of a medical probe in various branched organs, such as ENT, bronchoscopy, or neurology procedures.

System Description

Figure 1:
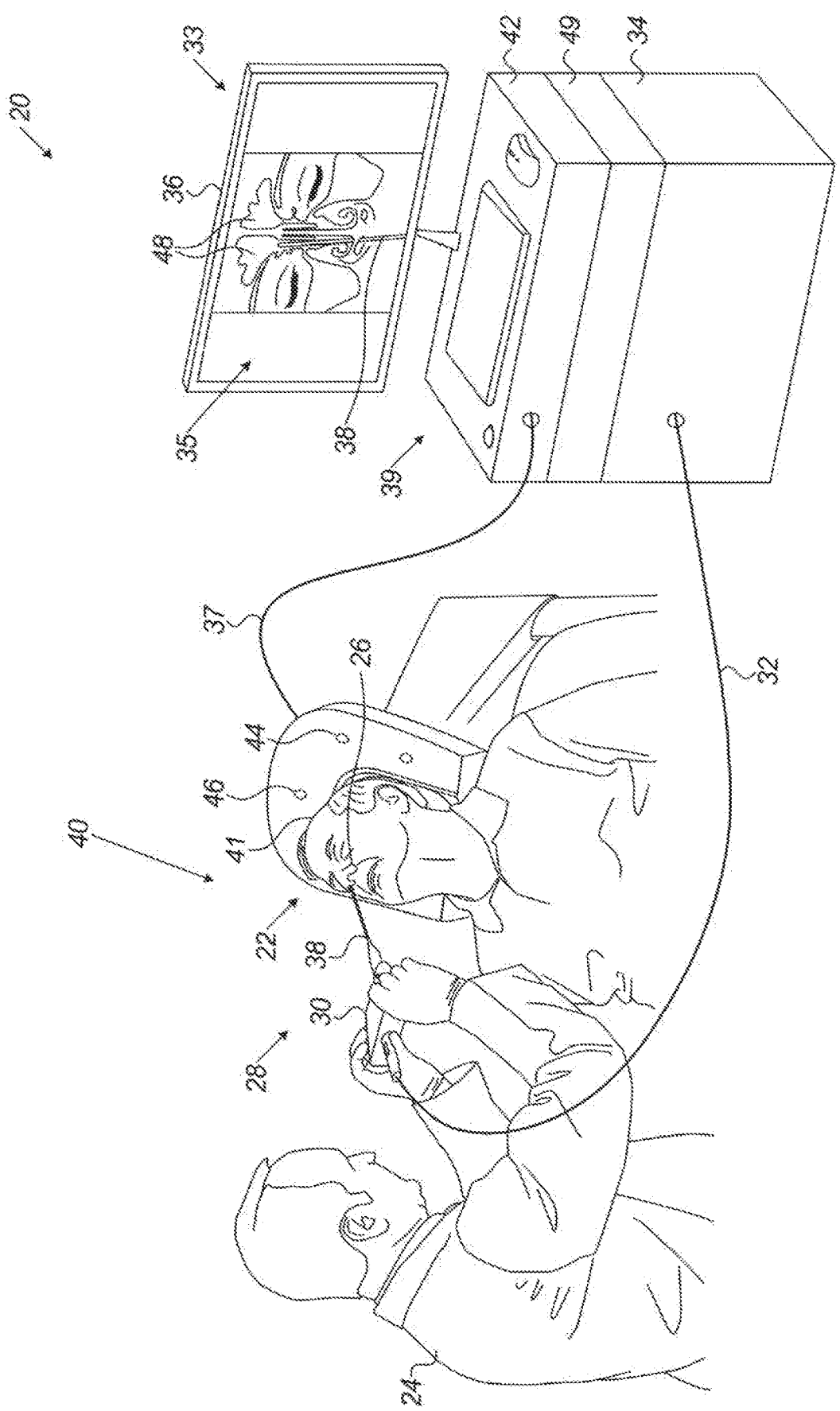
FIG. 1 is a schematic, pictorial illustration of an ear-nose-throat (ENT) procedure using an ENT system, in accordance with an embodiment of the present invention.

FIG. 1 is a schematic, pictorial illustration of an ear-nose-throat (ENT) procedure using an ENT system 20, in accordance with an embodiment of the present invention. In some embodiments, ENT system 20 comprises a medical probe, referred to herein as an ENT module 28, which is configured to carry out an ENT procedure, such as but not limited to treating infection from one or more sinuses 48 of a patient 22.

In some embodiments, ENT module 28 comprises a shaft 38, coupled to the distal end, which a physician 24 inserts into a nose 26 of patient 22. Module 28 further comprises a handheld apparatus 30, coupled to a proximal end of shaft 38 and configured to assist physician 24 in maneuvering the distal end of shaft 38 (shown in detail in FIGS. 2A and 2B below) in a head 41 of patient 22.

In an embodiment, system 20 further comprises a magnetic position tracking system, which is configured to track the position of one or more position sensors in head 41. The magnetic position tracking system comprises magnetic field-generators 44 and multiple position sensors (not shown). The position sensors generate position signals in response to sensing external magnetic fields generated by field generators 44, thereby enabling a processor 34 (described in detail below) to estimate the position of each sensor as will be described below.

This method of position sensing is implemented in various medical applications, for example, in the CARTO™ system, produced by Biosense Webster Inc. (Irvine, Calif) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004, 2003/0120150 A1, issued as U.S. Pat. No. 7,729,742 on Jun. 1, 2010 and 2004/006817 A1, whose disclosures are all incorporated herein by reference.

System 20 further comprises a location pad 40, which comprises field-generators 44 fixed on a frame 46. In the exemplary configuration shown in FIG. 1, pad 40 comprises five field-generators 44, but may alternatively comprise any other suitable number of generators 44. Pad 40 further comprises a pillow (not shown) placed under head 41 of patient 22, such that generators 44 are located at fixed, known positions external to head 41.

In some embodiments, system 20 comprises a console 33, which comprises a memory 49, and a driver circuit 42 configured to drive, via a cable 37, field-generators 44 with suitable signals so as to generate magnetic fields in a predefined working volume in space around head 41.

In some embodiments, console 33 comprises processor 34, typically a general-purpose computer, with suitable front end and interface circuits for receiving signals from tool 28 having multiple magnetic sensors (not shown) coupled thereto, via a cable 32, and for controlling other components of system 20 described herein.

In some embodiments, processor 34 is configured to estimate the position of each position sensor. Based on the estimated positions of the sensors, processor 34 is configured to derive the position, orientation and steering radius of curvature of the distal end of ENT tool 28 (shown in FIGS. 2A and 2B below) in the coordinate system of the magnetic position tracking system.

In the context of the present invention and in the claims, the terms "bending" "steering" are used interchangeably and refer to deflection of one or more sections of ENT tool 28 as will be described in detail in FIGS. 2A and 2B below.

In some embodiments, processor 34 is configured to receive via an interface (not shown), one or more anatomical images, such as computerized tomography (CT) images depicting respective segmented two-dimensional (2D) slices of head 41, obtained using an external CT system (not shown). The term "segmented" refers to displaying various types of tissues identified in each slice by measuring respective attenuation of the tissues in the CT system.

Console 33 further comprises input devices 39 for controlling the operation of the console, and a user display 36, which is configured to display the data (e.g., images) received from processor 34 and/or to display inputs inserted by a user using input devices 39 (e.g., by physician 24).

In some embodiments, processor 34 is configured to select one or mode slices from among the CT images, such as an image 35, and to display the selected slice on user display 36. In the example of FIG. 1, image 35 depicts a sectional front-view of one or more sinuses 48 of patient 22.

FIG. 1 shows only elements related to the disclosed techniques, for the sake of simplicity and clarity. System 20 typically comprises additional modules and elements that are not directly related to the disclosed techniques, and therefore, are intentionally omitted from FIG. 1 and from the corresponding description.

Processor 34 may be programmed in software to carry out the functions that are used by the system, and to store data in memory 49 to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

Steerable Distal-End Assembly Made from a Single Tube

Figure 2A:
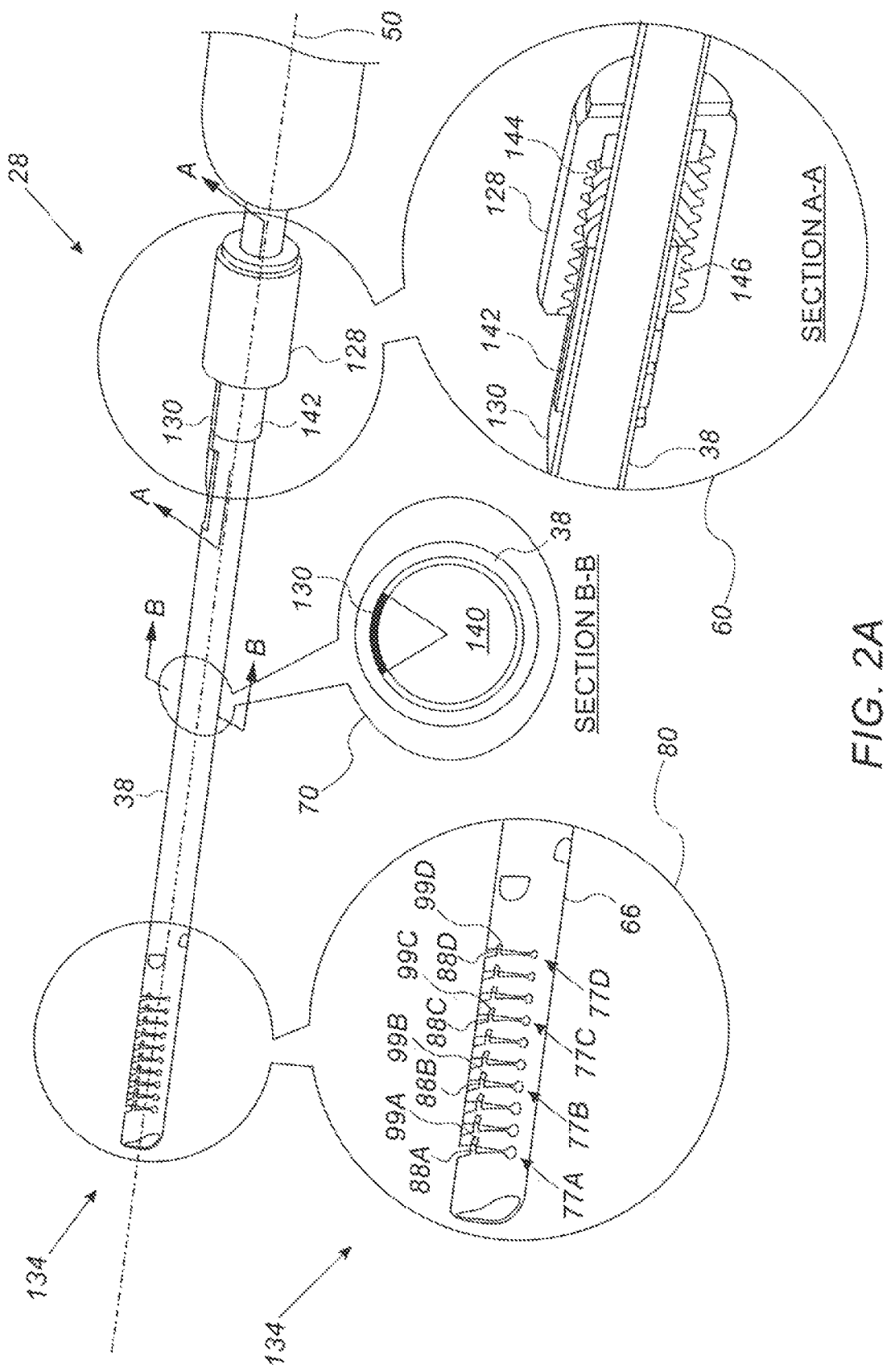
FIGS. 2A and 2B are schematic, pictorial illustrations of a medical probe having a steerable distal-end assembly, in accordance with embodiments of the present invention.

FIG. 2A is a schematic, pictorial illustration of ENT module 28 having a steerable distal-end assembly 134 in a straight position, in accordance with an embodiment of the present invention.

Reference is now made to an inset 80. In some embodiments, distal-end assembly 134 comprises a hollow tube 66, which is coupled to the distal end of shaft 38 and is typically made from a single piece of any suitable material, such as but not limited to a suitable alloy of nickel and titanium, e.g., Nitinol™ or super-elastic Nitinol™, having high repeatability.

In some embodiments, tube 66 is sized and shaped for being comfortably inserted through nose 26 into sinuses 48 or any other organ in head 41 of patient 22. Tube 66 is also sized and shaped for allowing a medical instrument, such as a sinuplasty balloon, a surgical tool, a suction or irrigation tool, or any other suitable tool, to be subsequently inserted through a lumen 140 of tube 66, which is described in detail below.

In some embodiments, tube 66 of distal-end assembly 134 has multiple openings, such as openings 77A, 77B, 77C and 77D, each of which formed at a respective section, also referred to herein as a rib, of distal-end assembly 134.

In the example of FIG. 2A, opening 77A is positioned at the distalmost of distal-end assembly 134 and has the largest size from among all openings 77A-77D. As will be depicted in FIG. 2B below, the opening size determines the bending limit of the respective section of distal-end assembly 134.

In some embodiments, each of openings 77A-77D has a slit, which may be formed, by laser cutting or using any other suitable technique, on a section of the circumference of tube 66. Each of the slits has an opening angle which depends on the width of the slit, as will be depicted in FIG. 2B below.

In some embodiments, opening 77A comprises an intrusion 99A, which is sized and shaped to fit snugly over a protrusion 88A of tube 66. Note that when distal-end assembly 134 is in a straight position, also referred to herein as unflexed state, protrusion 88A and intrusion 99A are typically disengaged from one another and opening 77A has the maximal size, e.g., along a longitudinal axis 50.

In some embodiments, openings 77B, 77C and 77D comprise respective intrusions 99B, 99C and 99D, which is sized and shaped to fit snugly over respective protrusions 88B, 88C and 88D of tube 66. Note that opening 77D is the proximal most, along longitudinal axis 50, and has the smallest size from among openings 77A-77D. In such embodiments, the size of openings 77A-77D is gradually increasing with the proximity to the distal end of tube 66. For example, intrusion 99A is the largest from among all intrusions 99B-99D, and intrusion 99B is larger than intrusion 99C, which is larger than intrusion 99D. Similarly, protrusion 88A has the largest size from among protrusions 88A-88D, and the size of protrusions 88B-88D decreases along longitudinal axis 50, toward the proximal end of tube 66, such that protrusion 88D has the smallest size from among protrusions 88A-88D.

In the example configuration of FIG. 2A, tube 66 has ten openings, but in other configurations tube 66 may have any suitable number of openings, e.g., between 3 and 20 openings having any suitable size shape. Note that the openings may have a similar shape and different size, or a different shape, or any suitable combination of the above.

In alternative embodiments, the size of the openings may gradually increase from the proximal end to the distal end. For example, opening 77D, intrusion 99D and protrusion 88D may be larger than opening 77C, intrusion 99C and protrusion 88C, respectively. Similarly, opening 77C, intrusion 99C and protrusion 88C may be larger than opening 77A, intrusion 99A and protrusion 88A, respectively.

In other embodiments, the size of openings may alter along longitudinal axis 50. For example, opening 77A, intrusion 99A and protrusion 88A may be larger than opening 77B, intrusion 99B and protrusion 88B, respectively, but smaller than the size of opening 77C, intrusion 99C and protrusion 88C, respectively. In yet other embodiments, the size of the openings, protrusions and intrusions of tube may have any other suitable distribution along longitudinal axis 50.

Reference is now made back to the general view of FIG. 2A. In some embodiments, ENT module 28 comprises a control handle 128, which is coupled to handheld apparatus 30 shown in FIG. 1 above and is fitted at the proximal end of shaft 38. Control handle 128 is configured to bend and straighten distal-end assembly 134 relative to longitudinal axis 50 of ENT module 28.

Reference is now made to an inset 70, which is a traversing sectional view BB of shaft 38. In some embodiments, shaft 38 is hollow and shaped to define a tube lumen 140. ENT module 28 comprises a pull wire 130, made from or comprising a suitable alloy of nickel and titanium, such as Nitinol™ or other suitable materials, which passes proximally-distally through tube lumen 140.

In some embodiments, pull wire 130 may be connected to a ring or any other element coupled to a selected section, such as the distalmost section, of hollow tube 66, for example, distal to opening 77A. As described in FIG. 2B below, pull wire 130 facilitates adjusting the configuration of the distal portion of tube 66. In other embodiments, ENT module 28 may comprise a ribbon (not shown), instead of, or in addition to pull wire 130. The ribbon may comprise Nitinol™ or any other suitable material. A configuration of the aforementioned ribbon in an ENT tool is described in detail in U.S. Patent Application Publication 2017/0325841, issued as U.S. Pat. No. 10,820,923 on Nov. 3, 2020, which is incorporated herein by reference.

As shown in FIG. 2A, in the unflexed state of tube 66, each of the openings, and sections between the openings, is generally flush with its neighbors along axis 50 at the circumference of tube 66.

Reference is now made to an inset 60, which is a sectional view AA of control handle 128 along longitudinal axis 50. As described above, control handle 128 is fitted at the proximal end of shaft 38. In some embodiments, control handle 128 is turnable or rotatable and is configured to control pulling wire 130. As will be described in FIG. 2B below, by turning control handle 128 in one direction, pull wire 130 is pulled, thus causing flexion of distal-end assembly 134. Conversely, by turning control handle 128 in the opposite direction, pull wire 130 is pushed, thus causing tube 66 of distal-end assembly 134 to be unflexed and straight as shown in FIG. 2A. For example, the proximal end of pull wire 130 may be coupled to a sliding element 142, which is configured to slide between an extreme proximal position and an extreme distal position. By turning control handle 128, sliding element 142 is slid proximally or distally, thus causing tube 66 to be flexed or unflexed. In some embodiments, the inner surface of control handle 128 may be shaped to form a female threading 144, and control handle 128 may also comprise a complementary male threading 146, which is engaged with female threading 144. In an embodiment, when physician 24 (or any other operator of ENT module 28) turns control handle 130, male threading 146, which is coupled to sliding element 142, moves the sliding element proximally or distally along axis 50, and controls the state of tube 66 as described above.

This particular configuration of distal-end assembly 134 is shown by way of example, in order to illustrate certain problems that are addressed by embodiments of the present invention and to demonstrate the application of these embodiments in enhancing the performance of such a medical probe (e.g., ENT module 28). Embodiments of the present invention, however, are by no means limited to this specific sort of example configuration of ENT module, and the principles described herein may similarly be applied to other sorts of medical probes.

Controlling the Local Radius of Curvature of the Distal-End Assembly

Figure 2B:
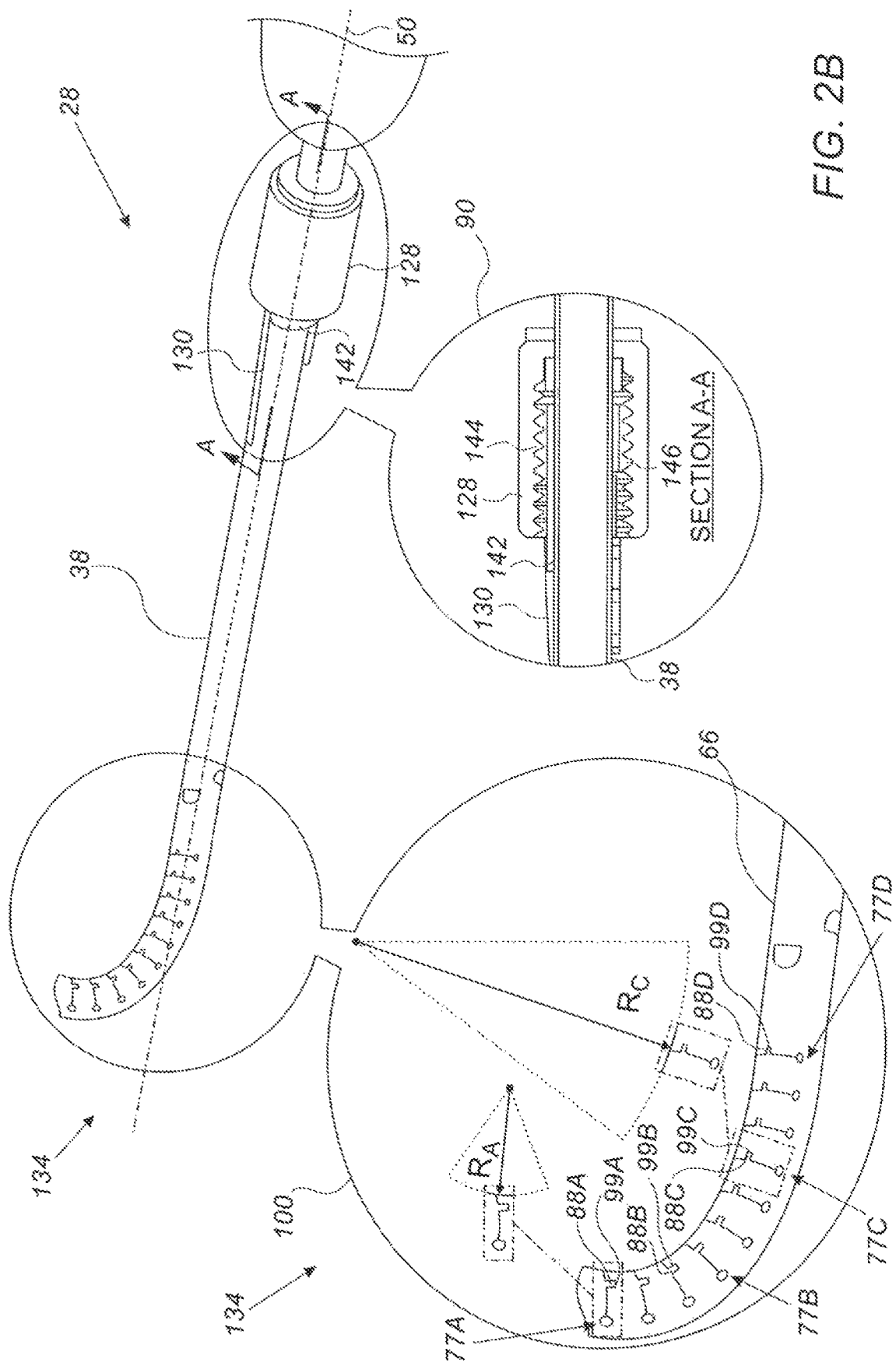

FIG. 2B is a schematic, pictorial illustration of ENT module 28 having distal-end assembly 134 in a steered position, in accordance with an embodiment of the present invention.

Reference is now made to an inset 90 showing a longitudinal cross-section of control handle 128. As described in FIG. 2A above, when physician 24 turns control handle 128, pull wire 130 is pulled along axis 50 towards the proximal end of ENT module 28, and tube 66 is steered, as shown in the general view of FIG. 2A. In some embodiments, control handle 128 is further configured, subsequently to the aforementioned turning, to hold the ribbon in place, thus to maintain the configuration of tube 66. For example, the engagement of threading 144 with threading 146, as shown in FIG. 2B, may prevent the sliding element from sliding.

In other embodiments, control handle 128 may comprise any other suitable mechanism for prevent undesired sliding of the aforementioned pull wire or ribbon or any other mechanism suitable for steering the distal-end assembly of the ENT tool.

Reference is now made to an inset 100 showing distal-end assembly 134 in a fully steered position. In some embodiments, when pull wire 130 is pulled proximally along axis 50, tube 66 is bending and the protrusions of tube 66 are inserted into the respective intrusions thereof. For example, protrusions 88A, 88B, 88C and 88D are inserted into intrusions 99A, 99B, 99C and 99D, respectively.

As described in FIG. 2A above, the openings, protrusions and intrusions of tube 66 may have different size, e.g., gradually increasing with the proximity to the distal end of tube 66. In the example shown in inset 100, opening 77A, protrusion 88A and intrusion 99A are the largest, and opening 77D, protrusion 88D and intrusion 99D are the smallest from among all openings, protrusions and intrusions of tube 66.

As described in FIG. 2A above, each of openings 77A-77D has a slit, formed on a section of the circumference of tube 66. The size (e.g., width) of the slit determines the opening angle when physician 24 is bending tube 66. In the example of FIG. 2B, the slit of opening 77A is larger than the slit of opening 77C, and therefore, the opening angle of opening 77A is larger than the opening angle of opening 77C. Note that in the unflexed state shown in FIG. 2A above, physician 24 is not bending tube 66 and therefore the sections of tube 66 remain flush with one another.

In some embodiments, the size of the slit of the opening, and the size of the protrusion and intrusion limit the bending of the respective section. The maximal bending ability at a given location along tube 66 may be specified by a local radius of curvature (LROC) at that location.

In such embodiments, a larger opening, protrusion and intrusion enable increased the amount of bending, measured by a smaller LROC. For example, opening 77A, protrusion 88A and intrusion 99A are larger than opening 77C, protrusion 88C and intrusion 99C. As shown in inset 100, $R_A$, which is the LROC of opening 77A is smaller than $R_C$, which is the LROC of opening 77C. Note that the term "local" refers to the arc formed by the bending of the outer surface of tube 66 at the position of the respective opening.

This configuration referring to the sizes of the remaining openings, intrusions and LROCs of tube 66 are within the ranges defined above between openings 77A and 77D. Note that the dimensions described above are provided by way of example, and in other embodiments, the openings, intrusions, protrusions and LROCs may have any other suitable dimensions.

Note that the LROCs described above are indicative of the LROC at a maximal bending of tube 66 at each respective section. In some embodiments, physician 24 may apply less bending to tube 66 by applying a smaller turning angle to control handle 128. In such embodiments, only a portion of the protrusion may be inserted into the respective intrusion, and the LROC may be larger compared to the fully steered LROC shown in inset 100.

In some embodiments, when physician 24 moves ENT module 28 in head 41 of patient 22, at least one section of tube 66 may by fully steered and another section may be partially steered or not steered at all. For example, physician 24 may position distal-end assembly 134 at the ostium of sinus 48 (as shown in FIG. 1 above), and subsequently steer only the third distalmost part of tube 66.

In this example embodiment, the ostium of sinus 48 may fix the sections of openings 77C and 77D to be substantially flush with shaft 38 (as shown in FIG. 2A above), physician 24 may partially steer the section of opening 77B (e.g., by having only part of protrusion 88B inserted into a respective part of intrusion 99B), and the section of openings 77A fully steered to obtain the $R_A$ LROC shown in inset 100 (e.g., protrusion 88A is fully inserted into intrusion 99A). In other example embodiments, physician 24 may partially or fully steer any other one or more sections of tube 66 so as to maneuver distal-end assembly 134 to a desired location in head 41, e.g., based on the tracked position of distal-end assembly 134 in image 35 shown in FIG. 1 above. Additionally or alternatively, physician 24 may rotate ENT module 28 about longitudinal axis 50, e.g., by rotating handheld apparatus 30, so as to improve the maneuverability for reaching the desired position at patient head 41.

Although the embodiments described herein mainly address medical probes used minimally invasive procedures carried out in the ear-nose-throat (ENT) of a patient, the methods and systems described herein can also be used in other applications, such as but not limited to in bronchoscopy or neurology procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
   (a) a body; and
   (b) a hollow shaft contiguously extending distally from the body, the hollow shaft comprising:
      (i) a plurality of openings positioned at various locations along a longitudinal axis of the hollow shaft, each opening having a size that limits bending of the hollow shaft by a local radius of curvature (LROC), the hollow shaft being longitudinally integral along the plurality of openings; and
      (ii) at least a portion of a linkage positioned within the distal end, passing proximally-distally, wherein the linkage is configured to bend the hollow shaft.

2. The apparatus of claim 1, wherein each opening of the plurality of openings comprises a slit having an opening angle.

3. The apparatus of claim 2, wherein each slit includes a radiused opening at each end of the slit.

4. The apparatus of claim 2, wherein each opening angle on the plurality of openings is at a different angle from any other opening angle on the hollow shaft.

5. The apparatus of claim 4, wherein each opening angle of the plurality of openings decreases from a proximal end of the hollow shaft to a distal most end.

6. The apparatus of claim 4, wherein each opening angle of the plurality of openings increases from a proximal end of the hollow shaft to a distal most end.

7. The apparatus of claim 1, wherein each opening comprises at least one intrusion and a corresponding protrusion, wherein each intrusion is configured to engage the corresponding protrusion when the hollow shaft is in a flexed position.

8. The apparatus of claim 7, wherein each intrusion from the plurality of openings has a different size from any other intrusion.

9. The apparatus of claim 7, wherein each intrusion and corresponding protrusion are configured to partially engage each other when in an unflexed state.

10. The apparatus of claim 1, wherein the hollow shaft is operable to transition between a flexed state and an unflexed state, wherein each opening of the plurality of openings is configured to have a minimal size in the flexed state, wherein each opening of the plurality of openings is configured to have a maximal size in the unflexed state.

11. The apparatus of claim 10, wherein the linkage is operable to transition the hollow shaft to either the flexed state or the unflexed state.

12. The apparatus of claim 1, wherein the linkage is coupled to a portion of the hollow shaft that is distal to a most proximal opening of the plurality of openings.

13. The apparatus of claim 1, wherein each of the openings of the plurality of openings is flush with any immediately adjacent opening along an axis at a circumference of the hollow shaft.

14. The apparatus of claim 1, wherein the hollow shaft comprises a shape memory alloy.

15. The apparatus of claim 1, wherein the hollow shaft is configured to be uncoupled from the body.

16. An apparatus comprising:
   (a) a body;
   (b) a contiguous hollow shaft comprising a series of openings along the circumference of the contiguous hollow shaft; and
   (c) a linkage positioned to extend from the body and to the series of openings, the linkage being configured to bend the hollow shaft,
   wherein each opening of the series of openings has an axial location along the contiguous hollow shaft that is different to any other opening of the series of openings,
   wherein at least one opening of the series of openings separately comprises at least one intrusion and a corresponding protrusion for every intrusion, and
   wherein each intrusion and corresponding protrusion are configured to engage each other when the contiguous hollow shaft is in a flexed state.

17. The apparatus of claim 16, the linkage being coupled to the contiguous hollow shaft for transitioning the contiguous hollow shaft to either the flexed state or an unflexed state.

18. The apparatus of claim 17, wherein each opening is in the same position radially along the contiguous hollow shaft.

19. A method for producing the apparatus of claim 1, the method comprising: providing the body and the hollow shaft for insertion into a cavity of a patient body.

20. The method according to claim 19, wherein each intrusion and corresponding protrusion are positioned and configured to engage each other when the contiguous hollow shaft is in a flexed state, wherein the method further comprises coupling the contiguous hollow shaft to a linkage, the linkage being operable to transition the contiguous hollow shaft between the flexed and an unflexed state.

* * * * *